United States Patent [19]

Wallshein

[11] 4,242,085
[45] Dec. 30, 1980

[54] MULTI-PURPOSE ORTHODONTIC BRACKET

[76] Inventor: Melvin Wallshein, 8645 Bay Pkwy., Brooklyn, N.Y. 11214

[21] Appl. No.: 959,671

[22] Filed: Nov. 13, 1978

[51] Int. Cl.³ .............................................. A61C 7/00
[52] U.S. Cl. ........................................ 433/14; 433/16
[58] Field of Search .......................... 32/14 A; 433/14

[56] References Cited

U.S. PATENT DOCUMENTS

| | | | |
|---|---|---|---|
| 3,435,527 | 4/1969 | Keshny | 32/14 A |
| 3,793,730 | 2/1974 | Begg et al. | 32/14 A |
| 3,975,824 | 8/1976 | Lee | 32/14 A |

Primary Examiner—Robert Peshock
Attorney, Agent, or Firm—Frishauf, Holtz, Goodman & Woodward

[57] ABSTRACT

A multi-purpose orthodontic bracket has first and second arch wire receiving openings formed therein, the first arch wire receiving opening being larger than the second arch wire receiving opening. An arch wire contact surface is defined over a minor portion of the width of the bracket and is in communication with the second arch wire receiving opening. A support is provided on at least one of the front and rear portions of the bracket for at least partially defining the first arch wire receiving opening, the support including at least a plurality of support areas distributed along at least a major portion of the width of the bracket for receiving and supporting an arch wire thereon. The bracket further includes a retaining pin receiving slot which extends substantially perpendicularly to the arch wire receiving openings. Further disclosed are retaining pin structures and a further novel bracket configuration which has an integral bent-up arch wire contact surface.

64 Claims, 47 Drawing Figures

MULTI-PURPOSE ORTHODONTIC BRACKET

BACKGROUND OF THE INVENTION

The present invention is directed to orthodontic brackets and, more particularly, to multi-purpose orthodontic brackets which may be made of metal, plastics, ceramics, glass ceramics, or any other suitable material.

Orthodontic brackets which are in widespread use today are generally either light wire brackets or edgewise-type brackets. Each of these types of brackets are suitable for specific orthodontic procedures.

An object of the present invention is to provide an improved orthodontic bracket which is a multi-purpose bracket which may be used as a light wire or edgewise bracket to enable, for example, an orthodontist to carry out a light-wire Begg-type technique and then proceed to an edgewise technique without requiring replacement of the bracket.

A further object of the invention is to provide such a bracket which is versatile, easy to use and easy to manufacture.

SUMMARY OF THE INVENTION

In accordance with the present invention, a multi-purpose orthodontic bracket comprises a rear portion adapted to be affixed to a surface of a tooth, a front portion and an intermediate portion interconnecting the front and rear portions. First and second arch wire receiving openings are formed in at least a surface of at least one of the front and rear portions, the first arch wire receiving opening being larger than the second arch wire receiving opening. An arch wire contact surface is defined over a minor portion of the width of the bracket and is in communication with the second arch wire receiving opening. Support means is provided on at least one of the front and rear portions of the bracket for at least partially defining the first arch wire receiving opening, the support means including at least a plurality of support areas distributed along at least a major portion of the width of the bracket for receiving and supporting an arch wire thereon. A retaining pin receiving slot in the bracket extends substantially perpendicular to the arch wire receiving openings.

In accordance with a further feature of the invention, improved retaining pins are provided for use with orthodontic brackets having an arch wire receiving opening and a pin retaining channel therein. The retaining pin comprising a shank for insertion in the pin receiving channel and a member extending transversely of the shank and defining an arch wire engaging and retaining surface for engaging a rectangular arch wire and for retaining the arch wire in the bracket with a predetermined orientation. In a preferred arrangement, the transverse member includes at least a part rectangular receiving surface which has at least two substantially parallel surfaces extending from the shank at a given angle whereby when a rectangular arch wire is received in the part rectangular receiving surfaces, a pre-torque may be applied to the arch wire relative to the bracket.

DETAILED DESCRIPTION

Referring to FIGS. 1-4, a first embodiment of a multi-purpose bracket according to the present invention is illustrated in the form particularly suitable for manufacture in plastics, ceramics, glass ceramics, or the like materials. The bracket comprises a rear surface 1 which is preferably contoured to better conform to the contour of a tooth to which the bracket is to be attached. The bracket preferably has a plurality of holes 2 formed in the rear surface thereof so as to enhance the adhesion of the bracket to a tooth by means of the appropriate adhesives. The number of holes 2 may be varied. Instead of holes, grooves or other irregularities may be formed on the rear surface 1. The holes, grooves or other irregularities are particularly important for direct bonding of the bracket to a tooth, but can be omitted when the brackets are secured with bands.

The bracket of FIGS. 1-4 further comprises an arch wire receiving channel 3, the channel 3 comprising first and second portions 4 and 5, respectively. The first arch wire receiving channel portion 4 is particularly useful for light wire type techniques and the second arch wire receiving channel portion 5 is particularly suitable for use in edgewise treatment techniques or other techniques using rectangular arch wires. A shelf arch wire support surface 6 is provided to separate the first and second arch wire receiving channel portions 4 and 5.

The first arch wire receiving channel portion 4 has a bearing surface 7 which approximates a "point contact" which is required for using the bracket as a light wire bracket. The bearing surface 7 is the upper portion of a generally triangular bracket portion 8 which interconnects the front and rear of the bracket. The bulk of interconnecting portion 8 is required to give the bracket suitable strength, especially when the bracket is made from materials such as plastics, ceramics, glass ceramics, or the like. When the bracket is fabricated from metal, it is not necessary that the connecting portion 8 have such extensive bulk.

The bracket further comprises an indentation 9 at both ends thereof for use in tying an arch wire to the bracket by means of ligature wire, or the like. When tying the arch wire to the bracket, the ligature wire is brought under the bracket through the indentation 9 so as to be positively retained relative to the bracket.

Figures 5, 6:
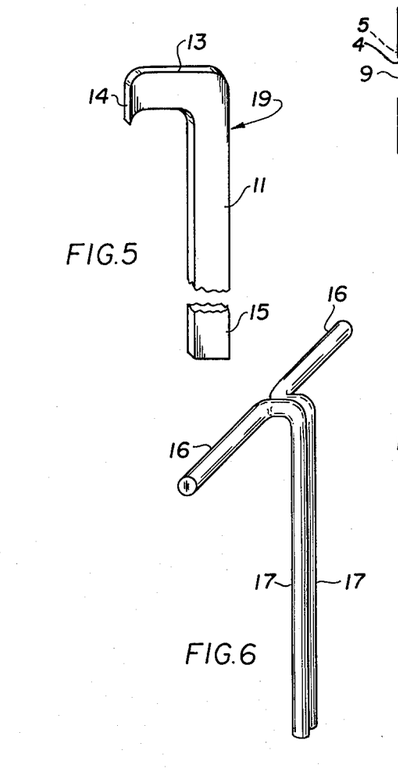
FIG. 5 is a perspective view of a pin for use in the embodiment of FIGS. 1-4, as well as in other embodiments of the invention.
FIG. 6 is a perspective view of another pin according to the invention.

When using the bracket of FIGS. 1-4 as a light wire bracket, the arch wire is dimensioned so as to fit within the first arch wire receiving channel portion 4 and an appropriate pin, such as that shown in FIG. 5 is inserted through the end portion 10 of the transverse slot 18 of the bracket so that the leg 11 of the pin 19 is received between the front wall 12 of the bracket and the arch wire which is inserted into opening 4. The top part 13 of the pin passes over the arch wire and the bent-down portion 14 enters behind the wire into the transverse slot of the bracket. The bottom portion 15 of the pin is bent over after it is fully inserted to retain the arch wire in the arch wire receiving opening 4.

Figure 7:
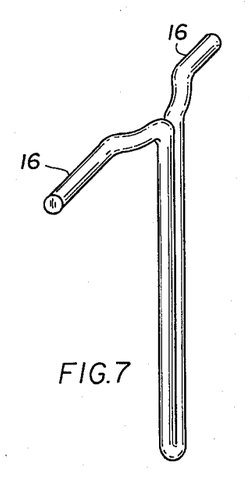
FIG. 7 is a perspective view of still another pin according to the invention.
Figure 8:
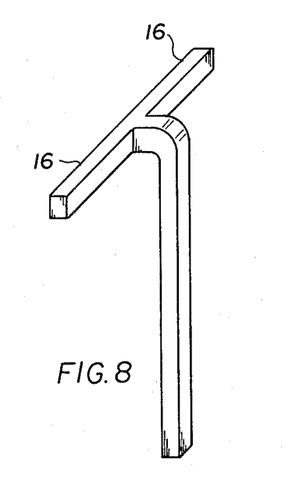
FIG. 8 is a perspective view of yet another pin according to the invention.

To use the bracket as an edgewise-type bracket, an arch wire, such as a round or rectangular arch wire, suitably dimensioned so as to fit into channel portion 5 and so as not to fall into channel portion 4, is inserted into the arch wire receiving channel so as to rest on shelf 6. Shelf 6 extends substantially along the whole length of the arch wire receiving opening 5. After insertion, the wire may be secured to the bracket by means of tying with ligature wire, or the like, or it may be secured in place by means of pin 19 of FIG. 5 or by special pins, such as those illustrated in FIGS. 6-8. The pins of FIGS. 6-8 operate similarly to that of FIG. 5 in that their bottom portions are bent over after they are completely inserted into the bracket to retain them in place. However, the pins of FIGS. 6-8 have wing portions 16 which lie over the top of the arch wire in order to more securely retain the arch wire in the opening 5 and to retain same against shelf 6 along substantially the complete length of the opening 5. In this manner, the arch wire can be used for applying torquing, tilting, uprighting, etc. forces to a tooth in a substantially conventional manner. The pins of FIGS. 6 and 7 are similar, except that the pin of FIG. 7 is fabricated from one bent piece of wire whereas the pin of FIG. 6 is fabricated from two pieces of wire which may be interconnected along the elongated leg portions 17, or which may be separately formed and individually inserted into the bracket.

Figure 9:
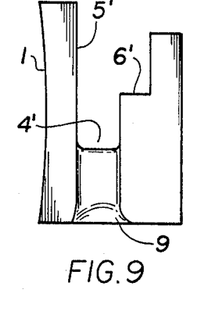
FIGS. 9, 10, 11 and 12 are side views of modifications of the embodiment of FIGS. 1-4.

FIG. 9 illustrates a modified bracket embodiment wherein the shelf 6' is located in only one wall of the bracket and the first and second arch wire receiving channel portions 4' and 5' share a common wall.

Figure 1:
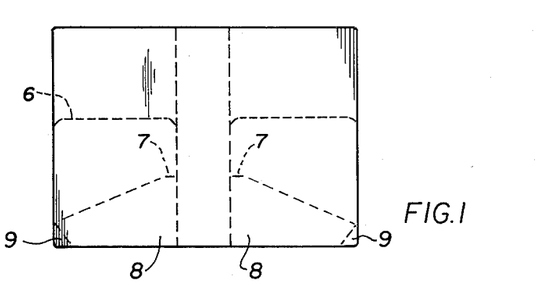
FIG. 1 is a front view of a first embodiment of the present invention.
Figure 10:
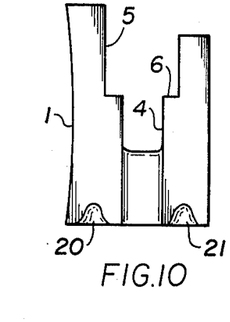

FIG. 10 illustrates a further modification of the embodiment of FIGS. 1-4 wherein the tying indentations 9 are replaced with respective indentations 20, 21 at the opposite ends of the bracket, similar to the manner shown in FIG. 1.

Figure 11:
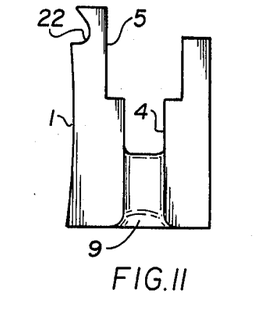

FIG. 11 illustrates a further modification wherein a notch 22 is formed in the rear surface 1 of the bracket to provide a further area for tying an arch wire to the bracket, for example by means of ligature wire, or the like. The tying indentation 9 of FIG. 11 may be replaced by the tying indentations 20 and 21 of FIG. 10, as desired. The arch wire receiving channels 5, 4 may be as shown in FIG. 9.

Figure 12:
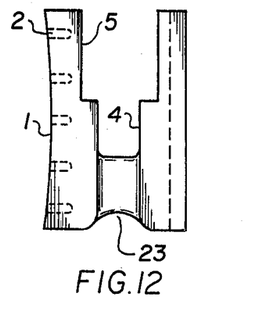

FIG. 12 illustrates a still further modification wherein a channel 23 extends along the complete length of the bracket for the purpose of receiving a tying wire, or the like. The channel 23 extending throughout the complete length of the bracket may be replaced by corresponding channels in the locations indicated by indentations 20 and 21 in FIG. 10.

Holes, slots, grooves, or the like may be used in the rear surfaces of the embodiments of FIGS. 9-12 to improve adhesion to the tooth, especially for direct bonding.

Figure 13:
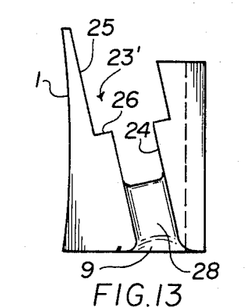
FIGS. 13 and 14 are side and front views, respectively, of a further modified bracket of the present invention.
Figure 14:
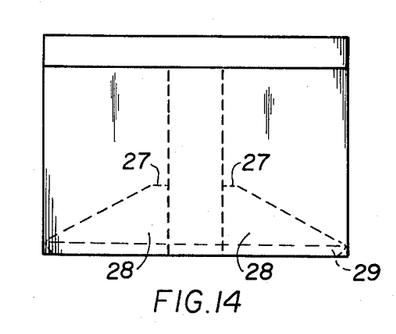
Figure 15:
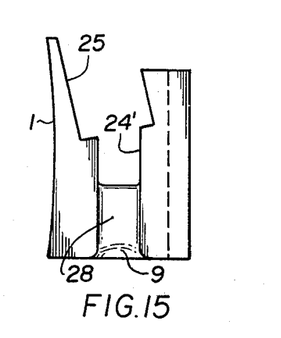
FIG. 15 is a side view of still another modified bracket of the present invention.
Figure 16:
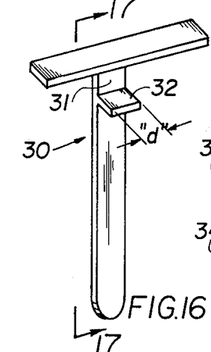
FIGS. 16 and 17 are perspective and sectional views respectively of a pre-torque pin of the invention.
Figures 17, 18, 19:
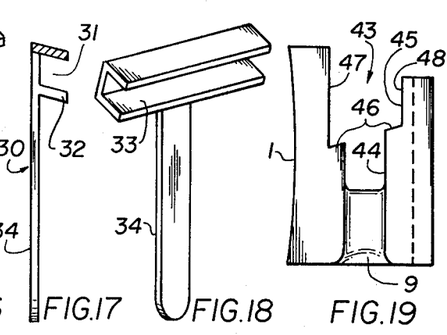
FIG. 18 is a perspective view of still another pin according to the invention.
FIG. 19 is a side view of still another modified bracket of the invention.

FIGS. 13 and 14 illustrate side and front views, respectively, of a further modification of the invention wherein the arch wire receiving channel 23' is oriented in an angular relation relative to the bracket. A ligature receiving channel 29 extends along the bottom of the bracket. The complete arch wire receiving channel 23', including first and second portions 24 and 25, respectively, may be angulated as illustrated in FIG. 13. Alternatively, the first arch wire receiving portion 24 (for use as a light wire bracket may be oriented vertically relative to the remainder of the bracket, while the second portion 25 of the arch wire receiving opening is angulated, as shown in FIG. 15. The angulated arch wire receiving openings 25, for use as an edgewise bracket, may be provided at any desired angle in order to provide a pre-torque to the arch wire for torquing a tooth. The arch wire may be retained in the arch wire receiving opening 25 by means of pins such as those shown in FIGS. 5-8, or a matching pre-torque pin 30, such as shown in FIGS. 16 and 17. The arch wire receiving channel 31 of the pin 30 is angulated to correspond to the angle of arch wire receiving channel 25 of FIGS. 13 and 15 so as to positively retain an arch wire againt the arch wire receiving shelf 26. The width "d" of bottom projecting portion 32 of the pin 30 corresponds preferably to the width of the slot 18 (see FIG. 3). This is to retain the pin relatively snugly in the bracket in the longitudinal direction thereof.

If it is desired to use a smaller arch wire in the arch wire receiving opening 25, then a pin such as that shown in FIG. 18 may be used. The pin of FIG. 18 is dimensioned so as to substantially fill the arch wire receiving opening 25 of the bracket, the arch wire being dimensioned to be snugly received within the arch wire receiving opening 33. The arch wire receiving opening 33 may be perpendicular to the bottom leg 34 of the pin (so as to be usable with a bracket such as that shown in FIGS. 1-4) or may be angulated to correspond to the angulation of arch wire receiving opening 25 in FIGS. 13 and 15. The angulation of the arch wire receiving opening may be different from that of the bracket arch wire opening—the pin retaining the arch wire in position. The bottom leg 34 of the pin is bent over after insertion into the bracket so as to retain the pin relative to the bracket.

The angulation of the arch wire receiving opening 33 of the pin of FIG. 18 may be in any direction. The angulation may be single (in one direction) or compound (in more than one direction), as discussed for example in connection with FIGS. 45-47.

FIG. 19 illustrates a further modification of the present invention wherein the side walls 47, 48 of the second arch wire receiving channel portion 45 are substantially vertical and the shelf walls 46 are angulated. The first arch wire receiving portion 44 is similar to that shown in FIG. 2. In use, the embodiment of FIG. 19 can receive a rectangular arch wire snugly between opposing walls 47, 48 and the arch wire is retained in a substantial horizontal-vertical orientation to the retention thereof by vertical walls 47, 48. The bracket of FIG. 19 can be used as a pre-torque bracket by using a slightly smaller rectangular wire which may tilt within the arch wire receiving opening 45 and lie on angulated shelf surface 46. A pin, preferably a pre-troque pin such as those shown in FIGS. 16, 17 and 18, is preferably used to retain the arch wire in a pre-torque condition against angulated shelf 46. A pre-torque pin can be used, of course, with a straight or angulated bracket channel.

In the embodiments of FIGS. 13, 14, 15 and 19, instead of pins to retain the arch wires in position, the arch wires may be tied by means of ligature wire, or the like, similar to the manner in which rectangular arch wires are tied to conventional edgewise brackets.

Figure 20:
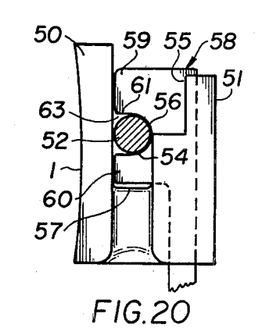
FIG. 20 is a side view of yet another modified bracket of the invention.

FIG. 20 illustrates a further modification of the invention wherein the rear wall 50 is higher than the front wall 51. The first arch wire receiving portion 54 (for use as a light wire bracket) has an arch wire 52 received therein. Instead of the arch wire 52 bearing against the bearing surface 57 of the bracket, a special pin 58 (shown in side elevation in FIG. 20) is inserted in the pin receiving slot 18 of the bracket. The pin 58 has an upper arch wire retaining projection 59 and a lower arch wire retaining projection 60 having a pointed upper surface 61. A substantially pointed upper surface 61 of the projection 60 of the pin 58 serves as the "point contact" for the light wire bracket. The internal bracket portion 8 (FIG. 1), 28, (FIG. 14) may be widened and made bulkier in order to provide stronger connection between the front and rear portions of the bracket so that a plastic, ceramic, or the like bracket may be stronger. Moreover, it is not necessary to provide the approximate point contact 7 (FIG. 3), 27 (FIG. 14) since the point contact may be provided by the point 61 of the pin 58.

Figure 2:
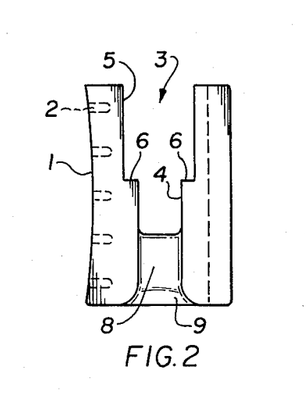
FIG. 2 is a left side view thereof.
Figure 3:
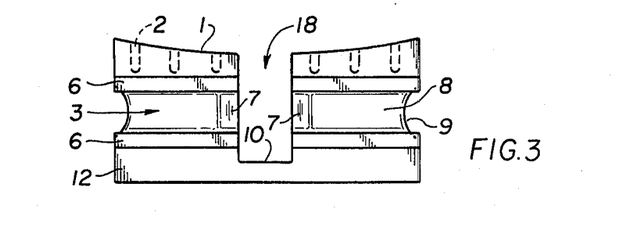
FIG. 3 is a top view thereof.
Figure 4:
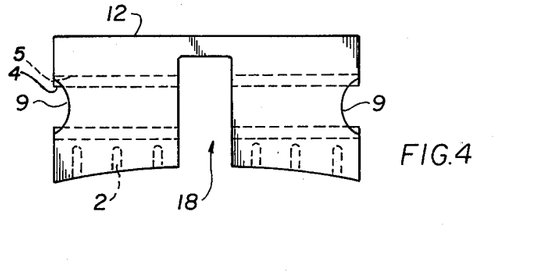
FIG. 4 is a bottom view thereof.
Figure 21:
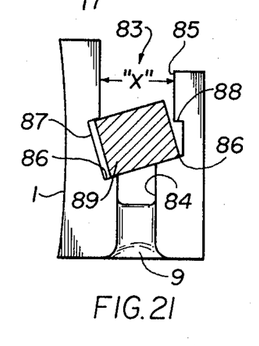
FIGS. 21 and 22 are side views of still further modified embodiments of the invention.

FIG. 21 illustrates a further modification of the invention wherein the arch wire receiving opening 83 has a first portion 84 similar to first portion 4 of FIG. 2 for using the bracket as a light wire bracket, and a second portion 85 for using the bracket as an edgewise-type bracket. The bracket further has a shelf portion 86 which is angulated relative to the horizontal. The second arch wire receiving opening 85 further has notch portions 87, 88 in the sides thereof for receiving an angulated arch wire 89 (shown in cross-section in FIG. 21). The width of the arch wire 89 substantially corresponds to the width "x" of the upper portion of the arch wire receiving channel 85. Therefore, when the arch wire 89 is placed in the channel 85 in the normal manner, it will remain with its side walls vertical and its top and bottom walls substantially horizontal. In order to provide a pre-torque to the arch wire 89, the arch wire may be forcibly snapped to an angulated orientation such as shown in FIG. 21 so that its left-hand upper corner snaps under the upper portion of the notch 87 and the right-hand lower corner of the wire is displaced into the notch 88. When the arch wire is released in this pre-torqued condition, it remains locked in the pre-torqued condition in the notch 87, for example as shown in FIG. 21. The notches may be substantially as shown in FIG. 21, may be pointed as shown in FIG. 22, or may take any other suitable shape.

Figure 22:
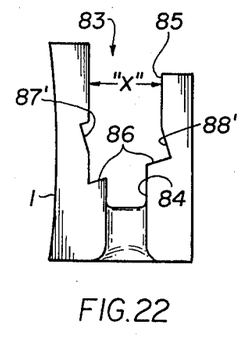

The vertical walls of the arch wire receiving channel portion 85 of FIGS. 21 and 22 may be made angulated, as shown in FIGS. 13 and 15. Retaining pins may be used to further aid in retaining the arch wire in place, the retaining pins taking any of the forms previously described and suitably shaped and dimensioned to retain the arch wire in position.

Figure 23:
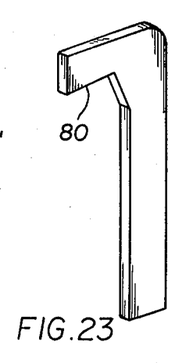
FIGS. 23 and 24 illustrate pins usable in the embodiments of FIGS. 21 and 22.
Figure 24:
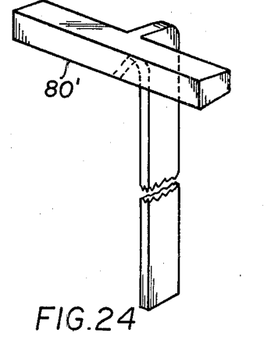

A pin of FIGS. 23 or 24 may be used to enhance retention of the arch wire in FIGS. 21 and 22. When using the pins of FIG. 23 or FIG. 24, the upper notches 87,87' may be omitted since the pins, with inclined surfaces 80,81', will retain the arch wire in position.

Figure 25:
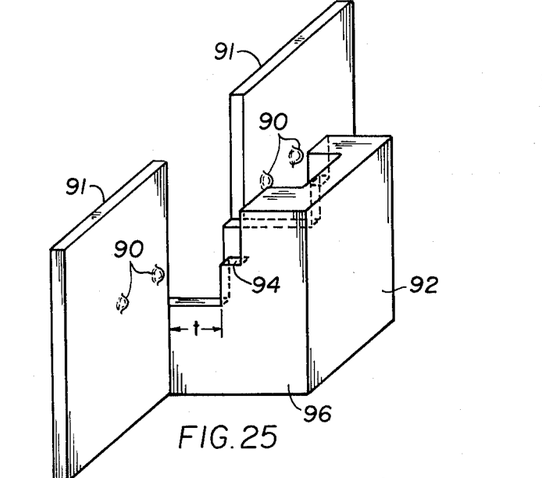
FIGS. 25 and 26 are perspective and side views, respectively, of a metallic bracket of the present invention.
Figure 26:
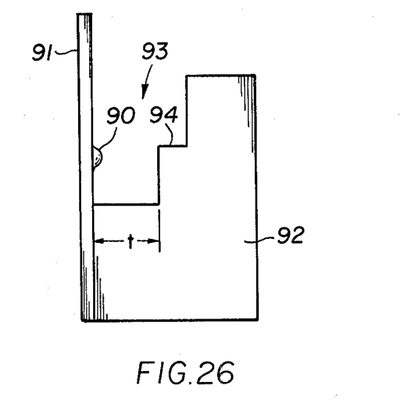

FIGS. 25 and 26 illustrate perspective and side views, respectively, of an embodiment of the invention fabricated in metal. In FIGS. 25 and 26, dimples or projections 90 spaced along the length of the arch wire receiving opening 93 serve as the "shelf" 6, for example of FIGS. 1-4, on which the arch wire rests when the bracket is used as an edgewise-type or heavy wire-type bracket. The front portion 92 of the bracket preferably has a step 94 formed therein on which a heavy wire may rest, similarly as in FIGS. 1-4. In some instances the dimples 90 may be omitted and the step 94 can provide sufficient support for an arch wire. The step 94 may be omitted in favor of dimples 90, or both may be provided as shown in FIGS. 25 and 26. Alternately the step or shelf 94 may be stamped in.

Figure 27:
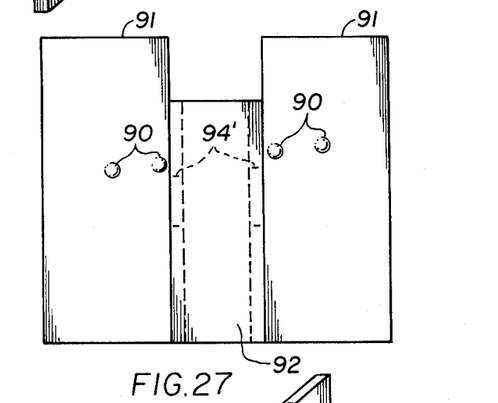
FIG. 27 is a front view of a modification of the bracket of FIGS. 25 and 26.
Figure 28:
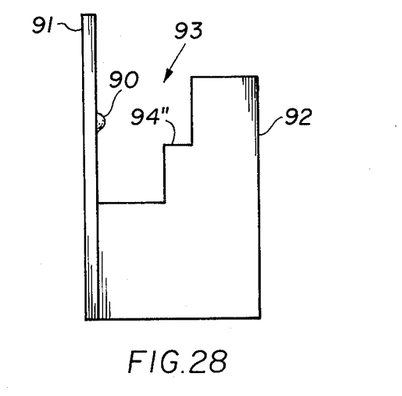
FIG. 28 is a side view of another modification of the bracket of FIGS. 25 and 26.

As seen in a front view of FIG. 27, the dimples 90 on the rear portion 91 of the bracket may be at different levels, so as to provide an angulated "shelf". The steps 94' may also be at corresponding different levels. As seen in FIG. 28, the dimples 90 may be on different levels than steps 94" to provide an angulated bracket similar in effect to that shown in FIG. 19. The brackets of FIGS. 25-28 may also include notches, such as notches 87, 88, 87' and 88' shown in FIGS. 21 and 22. In the metal configuration, it is not necessary to provide as large a central bracket portion 8 (FIG. 1), 28 (FIG. 14) since metal has sufficient strength and resistance to breakage without the provision of such large connecting portions between the front 92 and rear 91 portions of the bracket.

Figure 29:
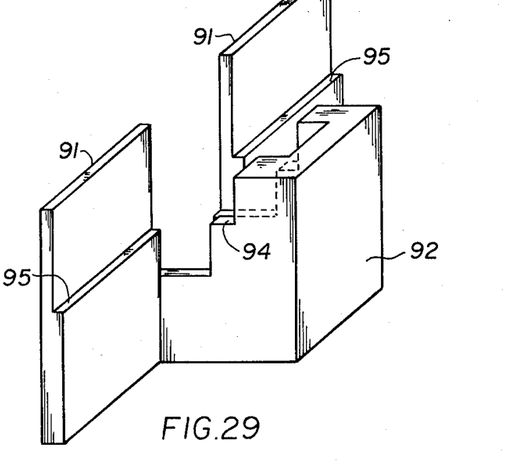
FIGS. 29 is a perspective view of an embodiment similar to that of FIG. 25, but wherein the dimples or projections are replaced by a groove in the rear portion of the bracket.

FIG. 29 illustrates a further modification of the present invention wherein a further step 95 is machined or otherwise formed in the rear portion of the bracket to substantially serve the same purpose as the dimples 90 of FIGS. 25-28. The shelf 95 may be machined in, for example, by a grinding operation on the rear portion 91 of the bracket. The shelf 95 may be formed at the same level as the shelf 94 or at a different level, similarly as in FIG. 28, or may be inclined to provide a similar effect as shown in FIG. 27.

Figure 30:
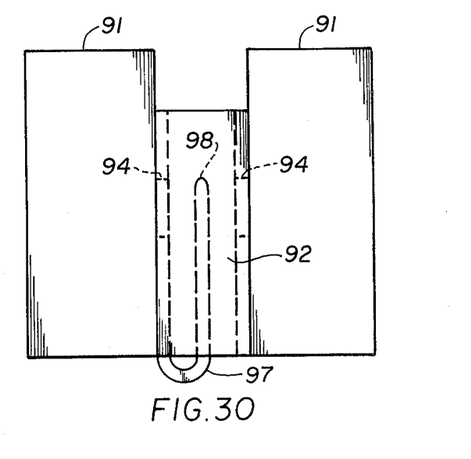
FIG. 30 is a front view of a modified bracket of the present invention.

FIG. 30 illustrates a further modification of the invention wherein a side wall 96 (see FIG. 25) has an integral tab portion 97 extending therefrom and which is bent around and upwardly as illustrated in FIG. 30. The tab 97 has, preferably, a rounded or sharp upper end 98 which serves as the contact point of the light wire bracket. The tab preferably has a width "t" (see FIGS. 25 and 26) so that the tab 97 is as wide as the width of the channel which receives the light wire. This is a particularly advantageous construction since the complete bracket may be made from bent metallic material as a unitary integral structure, since the end 98 of tab 97 will provide a highly desired point contact to provide improved results in the light wire orthodontic technique. The tab 97 may be provided, for example, in any of the embodiments of FIGS. 25-29.

Figure 31:
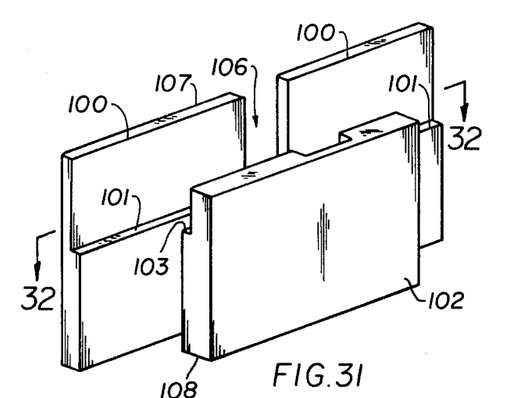
FIG. 31 is a perspective view of another bracket of the invention.
Figure 32:
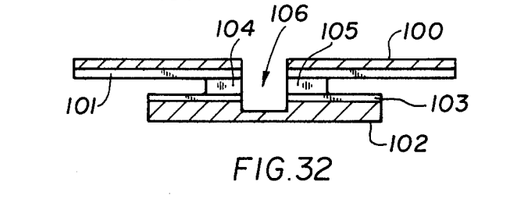
FIGS. 32 and 33 are sectional and side views, respectively of the bracket of FIG. 31.
Figure 33:
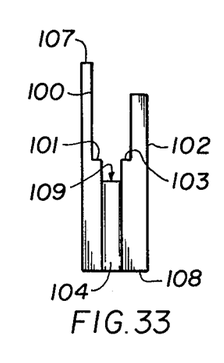

FIGS. 31, 32 and 33 are perspective, sectional and side views, respectively, of a further bracket of the present invention which may be advantageously machined or otherwise formed from metallic material, such as bar stock. The rear portion 100 of the bracket has a shelf or ledge 101 formed therein, for example by grinding the front portion of the rear portion 100. The front portion 102 has a shelf or ledge 103 formed therein which also may be formed by grinding, for example the same grinding operation that is used to form shelf 101. The front and rear portions are interconnected by central connecting portions 104,105 which also serve as the contact points for a light arch wire when the bracket is used in the light wire technique. The upper surfaces of portions 104,105 may be sharp or otherwise substantially pointed so as to provide a better "point contact" for a light arch wire. Alternatively, one of the central members 104,105 may be made higher than the other and preferably with a sharp or rounded point to provide a still further improved "point contact" for a light arch wire. The bracket further comprises a rear opening channel 106 for accommodating a locking pin, such as those pins discussed previously or which are otherwise well known in the art.

While the front portion 102 is shown as being not as wide as the rear portion 100, it should be clear that the front portion may be made wider, as desired. Also, the width and height of connecting members 104,105 may be varied, as desired, depending upon materials used and the application of the bracket. The ledges or steps 101,103 may be inclined, for example as shown in FIG. 27, or may be at different levels, for example as shown in FIG. 28.

In fabricating the bracket of FIGS. 31-33, the bar stock may already have the connecting portions 104,105 formed therein so that the bar stock looks substantially like an "I" beam. After the bar stock is cut in sections, for example along lines 107,108, a grinding wheel, for example, can be passed in a direction into the paper in FIG. 33 to simultaneously form ledges 101, 103 and cut out the central portion of the bracket so as to form the light wire receiving opening 109. In a second operation, the rear pin-receiving channel 106 can be formed by a grinding or other machining operation. The pin-receiving slot 106 may be formed in the bar stock before cutting into sections, after cutting into sections or before machining of the ledges 101,103.

Alternatively, the brackets of FIGS. 31-33 can be made by extrusion of elongated sections which are later cut up into individual bracket. The extrusion can be horizontally or vertically. In either case, later machining is carried out to form the structural features which could not be formed during extrusion. For example, vertical extrusion would result in "bar stock" similar to that discussed immediately hereinabove.

Figures 34, 35, 36, 37:
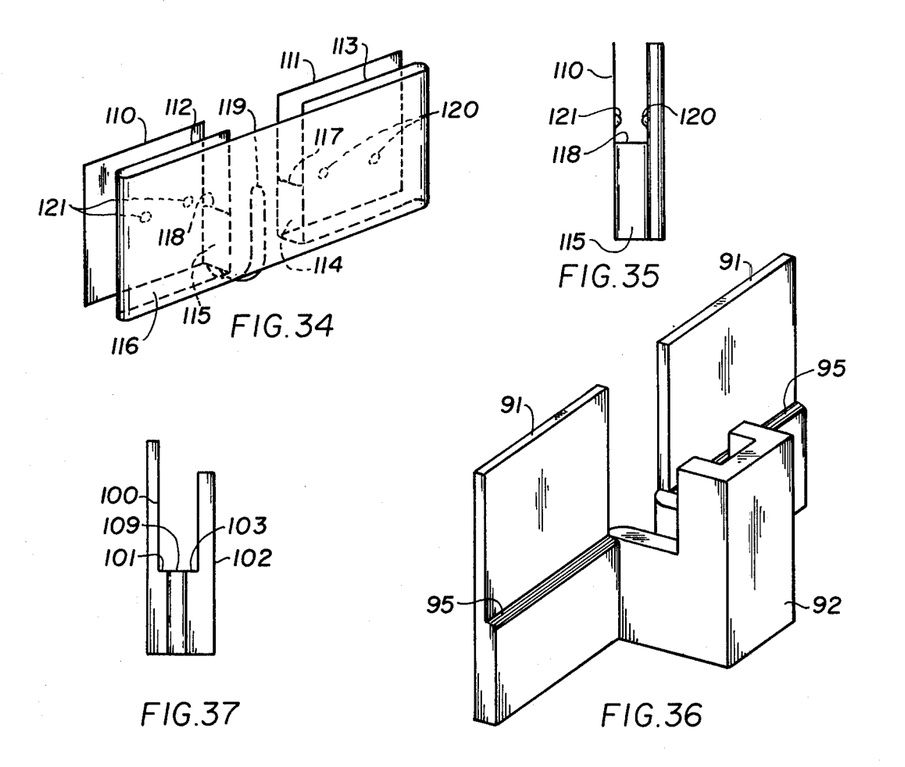
FIGS. 34 and 35 are perspective and side views, respectively, of another bracket of the present invention.
FIG. 36 is a perspective view of a modification of the bracket of FIG. 25.
FIG. 37 is a side view of a modification of the bracket of FIG. 33.

FIGS. 34 and 35 are perspective and left side views, respectively, of an embodiment which is suitable for manufacture from stamped and bent metallic sheet material. The bracket is a unitary, integral metallic structure. The bracket of FIGS. 34 and 35 comprises rear portions 110,111 which are integral with intermediate portions 112,113, respectively. Rear portion 111 is connected to intermediate portion 113 through an integral connecting portion 114. Rear portion 110 is connected to intermediate portion 112 with an integral connecting portion 115. A front portion 116 interconnects the remote ends of intermediate portions 112,113 and forms the front of the bracket. Rear portions 110,111 are adapted to be secured to a tooth, either directly, or through the intermediate of bands or other interconnecting devices. Rear portions 110,111 may have holes therein, or the like, for "direct bonding" use. The upper surfaces 117,118 of connecting members 114,115, respectively serve as the "point contact" means for a light wire technique. One of the edges 117,118 may be formed higher than the other to improve the sharpness of the "point contact" and/or one of the interconnecting members 114,115 may have a lower tab 119 which is bent upwardly to form the point contact surface in a manner similar to the tab 97 of FIG. 30. The intermediate portions 112,113 may have dimples or projections formed therein to serve the purposes of the steps, shelves or dimples previously described, and the rear portions 110,111 preferably has similar dimples or projections 121 formed therein either opposing dimples or projections 120 or at a different level therefrom. The side view of FIG. 35 is enlarged with respect to FIG. 34 for clarity. FIGS. 34 and 35 are line drawings for ease of illustration. It should be clear, however, that the members 110-118 have thickness. For example, the bracket may be fabricated of a bent stamped piece of metal which is, for example about 0.015 inches thick. If thick metal is used, it is possible to grind a portion of the facing surfaces of rear portion 110,111 and intermediate portion 112,113 to form steps or ledges, such as those shown in FIG. 31, in place of the dimples or projections 120,121.

In any of the embodiments of the bracket of the present invention, the shelf or step for supporting the rectangular arch wire or heavy arch wire may be formed at the same level as the "point-contact" surface which is used in practicing the light wire technique. Such an embodiment is shown, for example in FIG. 36. The FIG. 36 embodiment is a modification of the embodiments of FIGS. 25 and 29.

FIG. 37 is a side view of a modification of the bracket of FIGS. 31-33 with the point contact surface 39 at the same level as the steps or ledges 101,103. In the FIG. 37 embodiment, the ledges or steps 101,103 preferably extend the complete width of the bracket. It should be clear that the other brackets of the present invention may be appropriately modified so that the point contact surface and the ledges, dimples or projection, etc., are at the same level.

Figures 38, 39, 41:
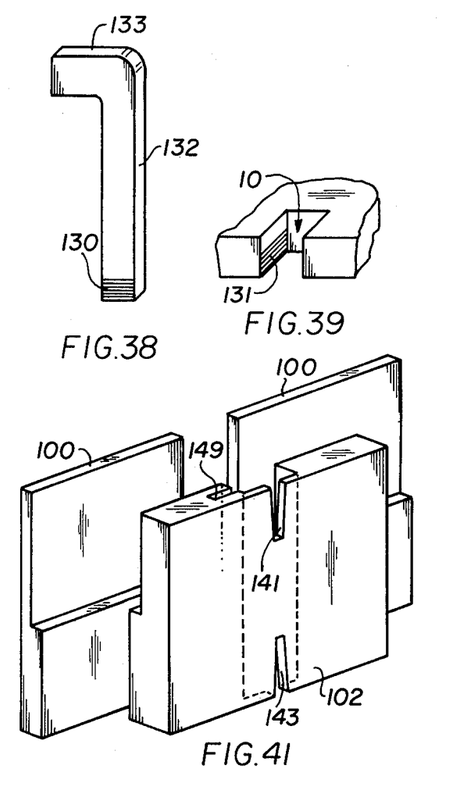
FIGS. 38 and 39 are perspective views of an arch wire locking pin and pin receiving channel, respectively, of the present invention.
FIG. 41 is a perspective view of a modified bracket of the present invention.

FIG. 38 illustrates a modified pin of the present invention which has serrations 130 on a lower surface portion of leg 132. The serrations preferably engage corresponding serrations or a projection on the associated surface or surfaces of a pin receiving channel 10 in the bracket so as to more securely retain the pin in the bracket. Pins having a serrated lower side surfaces 130, such as shown in FIG. 38, may be made of plastic and substantially eliminate the prior requirement of bending over the bottom of the pin after insertion in the channel so as to retain the pin in the channel of the bracket. The serrations 130 may project slightly from the side surfaces of the pin and may be slightly oversized relative to the pin receiving opening 10. In this case, the serrations can be easily forced through the pin receiving opening 10 and may "snap" over the lower surface of the bracket as the lower end of the pin projects out of the bottom of the bracket. This makes it difficult to remove the pin in the upward direction. The serrations may be replaced by projections serving the same purpose or the like. FIG. 39 illustrates a typical channel opening, such as opening 10 of FIG. 3, having serrations 131 therein for engaging the serrations 130 of the pin of FIG. 38. The serrations 130 may be on the rear surfaces 132, for example of the pin and/or the side surface or surfaces as shown in FIG. 38. Corresponding serrations or engagement means may then be provided in the pin receiving channel. The pin of FIG. 38, after insertion in a channel, will be difficult to remove in the upward direction.

The pins discussed above in relation to FIGS. 38 and 39 may be conveniently removed by clipping the top of the pin off and then pulling the pin downwardly through the channel in the direction of movement which is permitted by the ratchet or serrated surfaces, projections or the like. Other roughened or engaging surfaces for retention of the pin in the pin receiving opening may be provided in place of the serrated or ratchet-type surfaces illustrated in FIGS. 38 and 39.

Figure 40:
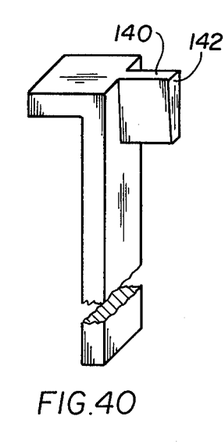
FIG. 40 is a perspective view of another arch wire locking pin of the invention.

FIG. 40 illustrates a further pin of the present invention having a stabilizing projection 140 extending, for example, from the rear surface thereof. The stabilizing projection may be received in, for example, a slot 141 formed in a bracket, such as shown in FIG. 41. The projection 140 preferably snugly and frictionally fits within the slot 141 to firmly lock the pin in position. This arrangement is particularly suitable for use with pins which are narrower than the width of the channel in which they are to be placed. This prevents the pin from moving in the mesially-distal direction. The projection 140 and receiving slot 141 technique can be used with any of the pins described herein in any of the brackets described herein, in any combination. The projection 140 and corresponding slot 141 can be used in combination with a serrated or ratchet-type arrangement of FIGS. 38 and 39, the projection 140 serving to prevent mesial-distal movement and the serrations or ratchet surfaces serving to prevent movement of the pin in the longitudinal direction of the shank of the pin. Preferably, the projection 140 is tapered so that its upper wider end 142 may be more advantageously received in a frictional engagement in the slot or opening 141 of the bracket. When the pin is fabricated of plastic materials, tight, frictional fits may be achieved due to the inherent resiliency of the plastic material from which the pin is made.

A similar slot 143 may be formed in the lower surface of the bracket, such as shown in FIG. 41, for engaging an auxiliary. The top notch 141 not only also accepts auxiliary, but also maintains the pin in a fixed position relative to the bracket, especially when the pin is smaller, for example narrower, than the channel in which the pin is received.

Figure 42:
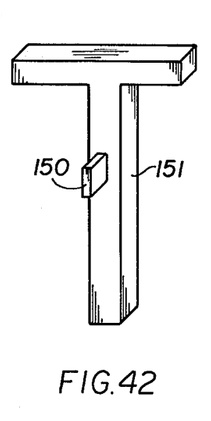
FIG. 42 is a perspective view of a modified pin of the present invention.

FIG. 42 illustrates a modified pin having a side projection 150 extending from the leg 151. The projection 150 is received in a corresponding slot (i.e., slot 149 in FIG. 41) formed in the pin receiving channel of the bracket, which slot may have a bottom surface against which projection 150 bottoms. Thus, projection 150 retains the pin at a predetermined relative height in the bracket and the pin is even more positively retained.

Figure 43:
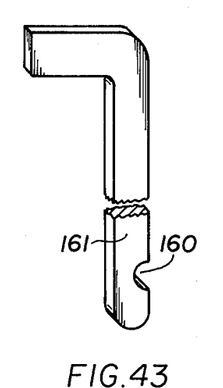
FIG. 43 is a side view of yet another modified pin of the invention.
Figure 44:
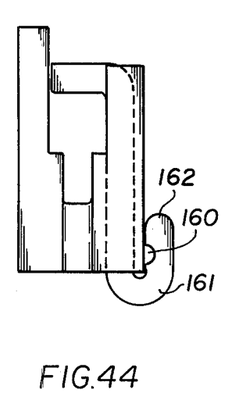
FIG. 44 is a side view showing the pin of FIG. 43 installed in the bracket of FIG. 41.

FIG. 43 illustrates a further modified pin having an opening 160 at the lower portion of the leg 161 thereof for engaging an arch wire, or the like. In use, the pin is inserted in the bracket, for example as shown in FIG. 44, with the lower end having the opening 160 therein extending below the bottom of the bracket. The lower end of the pin is then bent upwardly so that the opening 160 faces the front surface of the bracket so that an arch wire can be engaged in the opening 160, for example by snapping same into the opening 160 between the end 162 of the pin and the front face of the bracket. It is advantageous in this embodiment to provide a bracket with a lower slot 143 as shown in FIG. 41 so that the lower end of the pin may be bent upwardly through the slot 143 to further stabilize the bent up lower end of the pin. The opening 160 may be used for engagement with auxiliaries as well as arch wires.

Figure 45:
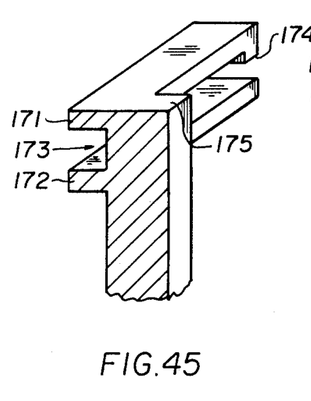
FIG. 45 is a sectional perspective view of another pin of the invention

FIG. 45 illustrates a sectional-perspective view of a further pin of the present invention which is similar to the pin of FIG. 18, but which effectively presents an inclined arch wire receiving channel. The pin has upper and lower members 171,172 which define an arch wire receiving channel 173 therebetween. The end of upper member 171 has a downward projection 174 which deflects the arch wire downwardly in the channel and therefore effectively "inclines" the arch wire in the channel 173. The pin is shown in partial section in FIG. 45 and preferably has extending members 171,172 extending to the left of the section plane by an amount substantially the same as that shown extending to the right. The channel 173 may be inclined in any other direction, as desired. The pin of 45 effectively converts a straight-channel bracket to an inclined or angulated channel bracket. Rearwardly extending portion 175 engages in the pin slot of the bracket so the extending members 171,172 are in registration with the arch wire receiving slot of the bracket.

Figure 46:
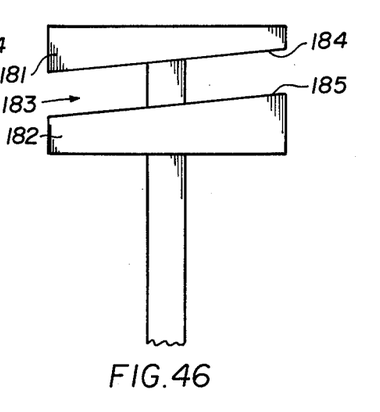
FIG. 46 is a front view of another pin of the invention.

FIG. 46 illustrates a further pin having an inclined arch wire receiving opening 183, the upper and lower extending members 181,182 having inclined surfaces 184,185, respectively, defining the inclined arch wire receiving opening 183.

Figure 47:
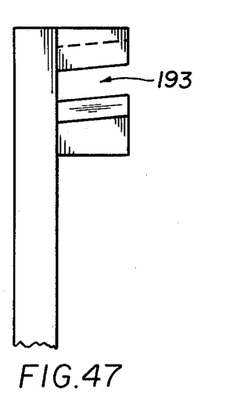
FIG. 47 is a left side view of a modified pin of FIG. 46, which exhibits a compound angulation.

FIG. 47 illustrates a modified pin which exhibits a compound angulation (that is, angulation in more than one direction). FIG. 47 is a left side view of a modification of the pin of FIG. 46, the arch wire receiving opening slanting upwardly to the right as illustrated in FIG. 46, as well as being inclined as illustrated in FIG. 47.

As should be clear, the angulation of any of the pins of the present invention, and/or of the arch wire receiving openings can be in substantially any direction to provide the desired orthodontic forces.

The various features of the different embodiments shown in the drawings may be interchanged and combined in any suitable manner to provide brackets specific to particular applications. Additionally, while the edges and surface connecting portions are shown sharp in some cases, the edges and the corners are preferably rounded or otherwise contoured so as to provide better protection from breakage due to chewing on objects in the mouth, or the like, and to make the bracket easier to manufacture by molding techniques. Rounded corners and edges also increase the strength of the bracket, particularly when the bracket is made from plastics, ceramics, glass ceramics, or the like. Steps or shelves such as 6,6', 94,95, etc. may be slightly rounded also, for example as shown in FIG. 36. Ceramic materials which may be used are those described in my prior U.S. patent application Ser. No. (not yet assigned) filed Aug. 9, 1978, the entire contents of which is incorporated herein by reference. Tie wire grooves, or other tie wire engaging means for engaging tie wires, elastic tieing or securing devices, may be provided on any of the brackets.

I claim:

1. A multi-purpose orthodontic bracket comprising:
   a rear portion adapted to be mounted to a surface of a tooth, a front portion, and an intermediate portion interconnecting said front and rear portions;
   means forming first and second arch wire receiving openings in at least a surface of at least one of said front and rear portions, said first arch wire receiving opening being larger than the second arch wire receiving opening;
   means defining an arch wire contact surface over a minor portion of the width of the bracket and in communication with said second arch wire receiving opening;
   support means on at least one of said front and rear portions for at least partially defining said larger first arch wire receiving opening, said support means including at least a plurality of support areas distributed along at least a major portion of the width of the bracket for receiving an arch wire thereon; and
   means defining a retaining pin receiving slot in said bracket extending substantially perpendicularly to the arch wire receiving openings.

2. The bracket of claim 1 wherein said interconnecting intermediate portion of said bracket comprises at least a portion of said means defining said arch wire contact surface.

3. The bracket of claim 1 wherein said means defining an arch wire contact surface depends from said intermediate interconnecting portion.

4. The bracket of any one of claims 1, 2 or 3 wherein said arch wire contact surface is substantially a point contact surface.

5. The bracket of any one of claims 1, or 3 wherein said support means is at the same level in the vertical direction as said arch wire contact surface.

6. The bracket of claim 5 wherein said support means comprises at least one elongated ledge or shelf formed in at least one of said front and rear portions.

7. The bracket of claim 6 wherein said ledge or shelf is oriented at a predetermined angle.

8. The bracket of claim 6 including a ledge or shelf on both of said front and rear portions.

9. The bracket of claim 5 wherein said support means comprises a plurality of projections projecting from at least one of said front and rear portions.

10. The bracket of any of claims 1, 2 or 3 wherein said support means is at an elevated level with respect to said arch wire contact surface.

11. The bracket of claim 10 wherein said support means comprises at least one elongated ledge or shelf formed in at least one of said front and rear portions.

12. The bracket of claim 10 wherein said ledge or shelf is oriented at a predetermined angle.

13. The bracket of claim 10 including a ledge or shelf on both of said front and rear portions.

14. The bracket of claim 10 wherein said support means comprises a plurality of projections projecting from at least one of said front and rear portions.

15. The bracket of claim 1 further comprising means defining at least one tie wire engaging slot or groove in said bracket.

16. The bracket of any one of claims 1, 2 or 3 wherein said means forming first and second arch wire receiving opening comprises wall portions, a first wall portion being formed in said front portion of said bracket and a second wall portion being formed in the rear portion of said bracket.

17. The bracket of claim 16 wherein said wall portions are substantially parallel to the rear surface of said rear bracket portion.

18. The bracket of claim 16 wherein said wall portions are oriented at an angle relative to the rear surface of said rear bracket portion.

19. The bracket of claim 16 wherein said wall portions and said support means define a substantially rectangular arch wire receiving opening for substantially non-rotationally receiving and retaining a rectangular arch wire.

20. The bracket of claim 19 wherein said wall portions and support means define an angulated substantially rectangular arch wire receiving opening.

21. The bracket of claim 19 further comprising a retaining pin adapted to be received in said retaining pin slot, said retaining pin having means thereon extending over a substantial portion of the length of said arch wire receiving opening to securely retain an arch wire received therein.

22. The bracket of claim 21 wherein said pin presents at least one angulated surface for retaining an arch wire in said angulated arch wire receiving opening in an angulated orientation.

23. The bracket of claim 22 wherein said pin includes an elongated arch wire receiving slot therein and defining at least a part-rectangular opening for receiving and retaining a substantially rectangular arch wire therein.

24. The bracket of claim 23 wherein said arch wire receiving opening of said pin is angulated in a predetermined direction.

25. The bracket of claim 16 comprising a retaining notch in at least one of said wall portions for receiving at least a portion of a rectangular arch wire for retaining a rectangular arch wire in an angulated condition in said first arch wire receiving opening.

26. The bracket of claim 20 further comprising a retaining pin adapted to be received in said retaining pin slot, said retaining pin having at least one angulated surface for retaining an arch wire in said angulated arch wire receiving opening in an angulated orientation.

27. The bracket of claim 26 wherein said pin includes an arch wire receiving slot therein and defining at least a part-rectangular angulated opening for receiving and retaining a substantially rectangular arch wire therein.

28. The bracket of claim 1, further comprising a retaining pin adapted to be received in said retaining pin slot, said retaining pin having an angulated surface which extends substantially across said first arch wire receiving opening for retaining a substantially rectangular arch wire in said first arch wire opening in an angulated orientation relative to said bracket.

29. The bracket of claim 28 wherein said pin includes an arch wire receiving slot therein defining at least a part-rectangular angulated opening for receiving and retaining a substantially rectangular arch wire therein.

30. The bracket of claim 28 wherein said at least one angulated surface of said pin extends over a substantial length of said at least one arch wire receiving opening.

31. The bracket of claim 28 wherein said angulation of said pin is about the longitudinal axis of said first arch wire receiving opening.

32. The bracket of claim 31 wherein said angulated surface of said pin is angulated in a mesial-distal direction.

33. The bracket of claim 28 wherein said angulated surface of said pin is angulated in a mesial-distal direction.

34. The bracket of claim 1, further comprising a retaining pin adapted to be received in said pin receiving slot, said pin having engaging means at the lower end thereof and said bracket having complementary engaging means at the lower end thereof which is adapted to be engaged by said engaging means of said pin when said pin is inserted in said slot, to thereby retain said pin in said slot.

35. The bracket of claim 34 wherein said engaging means comprises irregular surfaces on said pin and bracket.

36. The bracket of claim 1 further comprising a notch formed in the front portion of said bracket in communication with said pin receiving slot.

37. The bracket of claim 36 further comprising a retaining pin adapted to be received in said pin receiving slot, said retaining pin having projection means thereon adapted to be received in said notch in said front portion.

38. The bracket of claim 37 wherein said notch is a bottomed notch and limits the penetration of said pin in said pin receiving slot.

39. The bracket of claim 1 further comprising a notch extending upwardly from the bottom of said front portion and in communication with said pin receiving slot.

40. The bracket of claim 39 further comprising a retaining pin adapted to be received in said pin receiving slot and including an elongated lower leg which is engageable in said notch.

41. The bracket of claim 40 wherein said elongated lower leg extends below the lower edge of said bracket when said pin is fully received in said pin receiving slot and is bendable so as to be engaged in said notch.

42. The bracket of claim 41 wherein said elongated lower leg portion of said pin includes means for engaging an auxiliary orthodontic apparatus.

43. The bracket of claim 1 further comprising a retaining pin adapted to be received in said pin receiving slot, said pin having an elongated lower leg portion which is adapted to extend out of the bottom of said bracket when said pin is fully received in said bracket, said lower leg portion being bendable upwardly relative to said bracket.

44. The bracket of claim 43 wherein said bendable lower leg portion includes means for engaging an auxiliary orthodontic device.

45. The bracket of claim 1 further comprising a retaining pin adapted to be received in said pin receiving slot, said pin having an elongated lower leg portion which is adapted to extend out of the bottom of said bracket when said pin is fully received in said bracket, said lower leg portion including means for engaging an auxiliary orthodontic device.

46. The bracket of claim 1 wherein said bracket is made of bent metal plate-like material.

47. The bracket of claim 46 wherein said means defining an arch wire contact surface over a minor portion of the width of the bracket comprises a bent-over metal plate-like portion of said bracket which is integral with the intermediate portion of said bracket.

48. The bracket of claim 47 wherein said bent-over portion extends from the lower surface of said intermediate portion of said bracket and is bent upwardly so as to extend to said second arch wire receiving opening, the resulting upper edge of said bent-over portion defining said arch wire contact surface.

49. The bracket of either of claims 46 or 48 wherein said intermediate portion of said bracket is integral with said front and rear portions and extends between said front and rear portions, said intermediate portion having a stepped surface, the step of which defines said support means which at least partially defines said larger first arch wire receiving opening.

50. In combination, a retaining and an orthodontic bracket, said bracket having an arch wire receiving opening and a pin retaining channel therein, the pin comprising:
a shank for insertion in said pin retaining channel of said bracket; and
a member extending transversely of said shank and defining a part rectangular receiving surface for engaging a rectangular arch wire, said part rectangular receiving surface including at least two substantially parallel surfaces extending from said shank at other than 90°, whereby when a rectangular arch wire is received in said part rectangular receiving surfaces at least one of a pre-torque and an axial deviation is applied to said arch wire relative to said bracket.

51. The combination of claim 50 wherein said at least two substantially parallel surface of said part rectangular receiving surface of said retaining pin are angulated about the longitudinal axis of the arch wire received in said pin to impart a pre-torque to the arch wire.

52. The combination of either of claims 50 or 51 wherein said at least two substantially parallel surfaces are further angulated so that they extend at an angle of other than 180° to the mesial-distal plane which lies perpendicular to the longitudinal axis of a tooth to impart an axial deviation to the arch wire.

53. The combination of claim 50 wherein said part rectangular receiving surface includes at least three surfaces extending in the longitudinal direction of an arch wire, said three surfaces defining adjacent surfaces of a parallelogram, two of said surfaces opposing each other and being substantially parallel with each other.

54. The combination of claim 53 wherein said three surfaces define adjacent surfaces of a rectangle.

55. The combination of claim 50 wherein said transversely extending member extends from one end of said shank and the other end of said shank includes means for receiving auxiliary orthodontic devices.

56. In combination, a retaining pin and an orthodontic bracket, said bracket having an arch wire receiving opening and a pin retaining channel therein, the pin comprising:
a shank for insertion in said pin retaining channel of said bracket; and
a member extending substantially transversely of said shank at one end of said shank and defining an arch wire engaging surface for engaging an elongated side wall of a rectangular arch wire, said arch wire engaging surface being at an angle of other than 90° relative to said shank to retain a rectangular arch wire in an angulated condition in a bracket.

57. The combination of claim 56 wherein said arch wire engaging surface is angulated about the longitudinal axis of an arch wire to impart a pre-torque to an arch wire received in said pin.

58. The combination of either of claims 56 or 57 wherein said arch wire engaging surface is angulated so that it extends at an angle of other than 180° to the mesial-distal plane which lies perpendicular to the longitudinal axis of a tooth to impart an axial deviation to an arch wire received in said pin.

59. The combination of any one of claims 56 or 57 wherein said member defines an elongated engaging surface extending from said shank in the longitudinal direction of an arch wire.

60. The bracket of any one of claims 1, 2 or 3, further comprising in combination a retaining pin adapted to be received in said retaining pin receiving slot, said retaining pin having surface means thereon for engaging an arch wire and for retaining said arch wire in said arch wire receiving opening in an angulated stressed condition.

61. An orthodontic bracket comprising:
a rear portion adapted to be mounted to a surface of a tooth, a front portion, and an intermediate portion interconnecting said front and rear portions;
means forming at least one arch wire receiving opening between said front and rear portions;
means defining an arch wire contact surface over a minor portion of the width of the bracket and in communication with said arch wire receiving opening, said contact surface defining means including a bent-over integral portion of said bracket an end portion of which extends into communication with said arch wire receiving opening, said end portion at least partially defining said contact surface; and
means defining a retaining pin receiving slot in said bracket extending substantially perpendicularly to the arch wire receiving opening.

62. The bracket of claim 61 wherein said bent-over portion is integral with said intermediate portion.

63. The bracket of claim 62 wherein said bent-over portion extends from the lower surface of said intermediate portion of said bracket and is bent upwardly so as to extend to said second arch wire receiving opening, the resulting upper end portion of said bent-over portion defining said arch wire contact surface.

64. The bracket of any one of claims 61, 62 or 63, wherein said bracket is made of bent metal plate-like material.

* * * * *